US006083729A

United States Patent [19]
Martin et al.

[11] Patent Number: 6,083,729
[45] Date of Patent: Jul. 4, 2000

[54] METHODS FOR ISOLATING POLYHYDROXYALKANOATES FROM PLANTS

[75] Inventors: David P. Martin; Oliver P. Peoples, both of Arlington; Simon F. Williams, Sherborn, all of Mass.

[73] Assignee: Metabolix, Inc., Cambridge, Mass.

[21] Appl. No.: 08/548,840

[22] Filed: Oct. 26, 1995

[51] Int. Cl.⁷ .............................. C12P 7/62; C12P 7/40; C08G 63/06; C07C 69/66
[52] U.S. Cl. .................... 435/135; 435/136; 528/354; 528/358; 528/361; 560/185
[58] Field of Search .................. 435/135, 136; 528/361, 354, 358; 560/185

[56] References Cited

U.S. PATENT DOCUMENTS

| 5,229,279 | 7/1993 | Peoples et al. |
| 5,245,023 | 9/1993 | Peoples et al. |
| 5,250,430 | 10/1993 | Peoples et al. |
| 5,821,299 | 10/1998 | Noda ................................ 435/135 |

FOREIGN PATENT DOCUMENTS

| WO 91/00917 | 1/1991 | WIPO . |
| WO 92/19747 | 11/1992 | WIPO . |
| WO 93/02187 | 2/1993 | WIPO . |
| WO 93/02194 | 2/1993 | WIPO . |
| WO 93/11656 | 6/1993 | WIPO . |
| WO 94/07940 | 4/1994 | WIPO . |
| WO 94/11519 | 5/1994 | WIPO . |
| WO 94/12014 | 6/1994 | WIPO . |
| WO 94/23027 | 10/1994 | WIPO . |
| 94/26917 | 11/1994 | WIPO . |
| WO 95/05472 | 2/1995 | WIPO . |
| WO 96/03468 | 2/1995 | WIPO . |
| WO 96/06179 | 2/1996 | WIPO . |

OTHER PUBLICATIONS

Byrom, "Miscellaneous Biomaterials", in *Biomaterials*, (D. Byrom, ed.) Chapter 8, pp. 333–359, (MacMillan Publishers, London, 1991).
Carr, "Processing of Oilseed Crops", *Oil Crops of the World*, Röbblen, et al., eds., Chapter 11, pp. 226–259 (McGraw–Hill Publishing Company, 1989).
De Smet, et al., "Characterization of Intracellular Inclusions Formed by *Pseudomonas olevorans* During Growth on Octane," *J. Bacteriol.* 154(1):870–878 (1983).
Gasser, et al., "Genetically Engineering Plants for Crop Improvement," *Science* 244:1293–1299 (1989).
Griesbeck, et al., "Einfache Umwandlung von (−)–(R)–3–Hydroxybuttersäure in das (+)–(S)–Enantiomere und dessen Lacton (−)–(S)–4–Methyloxetan–2–on," *Helv. Chim. Acta* 70:1320–1325 (1987).
Hocking, et al., "Biopolyesters," *Chemistry and Technology of Biodegradable Polymers*, Griffin, ed., Chapter 4, pp. 48–96, (Chapman and Hall, London, 1994).
Holmes, "Biologically Produced (R)–3–hydroxyalkanoate Polymers and Copolymers," *Developments in Crystalline Polymers*, (Bassett, ed.) vol. 1, pp. 1–65 (Elsevier, London, 1988).

Lafferty, et al., "Microbial Production of Poly–β–Hydroxybutyric Acid," *Biotechnology*, (Rehm, et al., eds.) Chapter 66, pp. 135–176 (Verlagsgesellschaft, Weinheim, 1988).
Lemoigne, et al., "Fermentation β–Hydroxybutyrique," *Annales des Fermentations* 5:527–536 (1925).
Liebersgesell, et al., "Cloning and nucleotide sequences of genes relevant for biosynthesis of poly(3–hydroxybutyric acid) in *Chromatium vinosum* strain D," *European J. Biochem.*, 209:135–150 (1992).
Liebersgesell, et al., "Cloning and molecular analysis of the poly(3–hydroxybutyric acid) biosynthetic genes of *Thiocystis violacea*," *Appl. Microbiol. Biotechnol.* 38:493–501 (1993).
Müller, et al., "Poly(hydroxyalkanoates): A Fifth Class of Physiologically Important Organic Biopolymers?" *Angew. Chem. Int. Ed. Engl.* 32:477–502 (1993).
Nawrath, et al., "Targeting of the polyhydroxybutyrate biosynthetic pathway to the plastids of *Arabidopsis thalians* results in high levels of polymer accumulation," *Proc. Natl. Acad. Sci. USA* 91:12760–12764 (1994).
Peoples, et al., "Poly–β–hydroxybutyrate Biosynthesis in *Alcaligenes eutrophus* H16: Characterization of the Genes Encoding β–Ketothiolase and Acetoacetyl–CoA Reductase," *J. Biol. Chem.* 264(26):15293–15297 (1989).
Peoples, et al., "Poly–β–hydroxybutryte (PHB) Biosynthesis in *Alcaligenes eutrophus* H16," *J. Biol. Chem.* 264(26):15298–15303 (1989).
Peoples, et al., "Polyhydroxybutyrate (PHB): A Model System for Biopolymer Engineering," *Prog. Biotechnol.* 3:51–56 (1987).
Peoples, et al., "Biosynthetic Thiolase from *Zoogloea ramigera*," *J. Biol. Chem.* 262(1):97–102 (1987).
Peoples, et al., "Fine structural analysis of the *Zoogloea ramigera phbA–phbB* locus encoding β–ketothiolase and acetoacetyl–CoA reductase: nucleotide sequence of phbB," *Molecular Microbiol.* 3(3):349–357 (1989).

(List continued on next page.)

*Primary Examiner*—Herbert J. Lilling
*Attorney, Agent, or Firm*—Arnall Golden & Gregory, LLP

[57] ABSTRACT

Methods are provided for separating polyhydroxyalkanoates ("PHAs") from plants, such as transgenic oil crop plants. The methods advantageously permit both the oil and the PHAs to be recovered from the plant biomass. To isolate the PHAs, in one embodiment, a biomass derived from an oil crop plant is pre-processed, for example by grinding, crushing or rolling. The oil then is extracted from the biomass with a first solvent in which the oil is soluble and in which the PHAs are not highly soluble to remove the oil. The biomass then can be extracted with a second solvent in which the PHA is soluble, to separate the PHA from the biomass. Alternatively, the PHA-containing biomass is treated with a chemical or biochemical agent, such as an enzyme, to chemically transform the PHA into a PHA derivative. The PHA derivative then is separated from the mixture using, for example, a physical separation process such as distillation, extraction or chromatography. Advantageously, using the method, the plant oils, the PHAs and PHA derivatives can be recovered and purified on a large scale from oil containing plants such as transgenic oil crop plants.

35 Claims, 3 Drawing Sheets

OTHER PUBLICATIONS

Plattner, et al., "Cyclisch Oligomers von(R)–3–Hydroxybuttersäuer: Herstellung und strukturelle Aspekte," *Helv. Chim. Acta* 76:2004–2033 (1993).

Poirier, et al., "Polyhydroxybutyrate, a Biodegradable Thermoplastic, Produced in Transgenic Plants," *Science* 256:520–523 (1992).

Poirier, et al., "Production of Polyhydroxyalkanoates, a Family of Biodegradable Plastics and Elastomers, in Bacteria and Plants," *Bio/Technol.* 13:142–150 (1995).

Salunkhe, et al., eds., *World Oilseeds: Chemistry, Technology, and Utilization*, (Van Nostrand Reinhol, New York, 1992) (Table of Contents only).

Schubert, et al., "Cloning of the *Alcaligense eutrophus* Genes for Synthesis of Poly–β–Hydroxybutyric Acid (PHB) and Synthesis of PHB in *Escherichia coli,*" *J. Bacteriol.* 170(12):5837–5847 (1988).

Seebach, et al., "Direct Degradation of the Biopolymer PO Hydroxybutyric Acid to (R)–3–Hydroxybutanoic Methyl Ester," *Org. Synth.* 71:39–47 (1992).

Seebach, et al., "Biological–Chemical Preparation of 3–Hydroxycarboxylic Acids and Their Use in EPC–Synthesis," in *Stereochemistry of Organic and Bioorganic Transformations*, (Bartmann, et al., eds.) pp. 85–126 (VCH, Weinheim, 1987).

Seebach, et al., "Synthesis of Linear Oligomers of (R)–3–Hydroxybutyrate and Solid–State Structural Investigations by Electron Microscopy and X–Ray Scattering," *Helv. Chim. Acta*, 77:1099–1123 (1994).

Seebach, et al., "Partial Depolymerization and Solubilization of Poly(R)–3–hydroxybutanoate) (PHB) and its Copolymer with (R)–3–Hydroxyvalerate (BIOPOL®) by Treatment with Li–Amides/LiCl in Tetrahydrofuran at Low Temperatures," *Chimia* 44:112–116 (1990).

Seebach, et al., "The Triolide of (R)–3–Hydroxybutric acid—Direct Preparation from Polyhydroxybutyrate and Formation of a Crown Estercarbonyl Complex with Na Ions," *Angew. Chem. Int. Ed. Eng.* 31(4):434–435 (1992).

Slater, et al., "Cloning and Expression in *Escherichia coli* of the *Alcaligenes eutrophus* H16 Poly–β–Hydroxybutyrate Biosynthetic Pathway," *J. Bacteriol.* 170(10):4431–4436 (1988).

Steinbüchel, et al. "Molecular basis for biosynthesis and accumulation of polyhyroxyalkanoic acids in bacteria," *FEMS Microbiology Reviews* 103:217–230 (1992).

Steinbüchel, "Polyhydroxyalkanoic Acids," in *Biomaterials*, (Byrom, ed.) Chapter 3, pp. 123–213 (MacMillan Publishers, London, 1991).

Watson, et al., eds., *Corn Chemistry and Technology*, (American Association of Cereal Chemists Inc., St. Paul, Minnesota, 1994) (Table of Contents only).

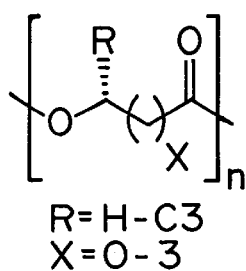
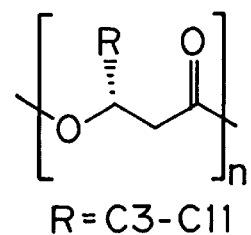
FIG. 1a
R=H-C3
X=0-3
FIG. 1b
R=C3-C11
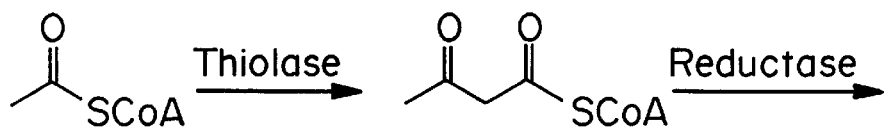
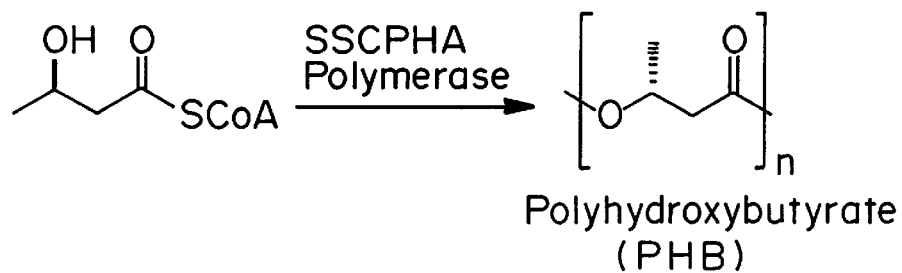
FIG. 2a
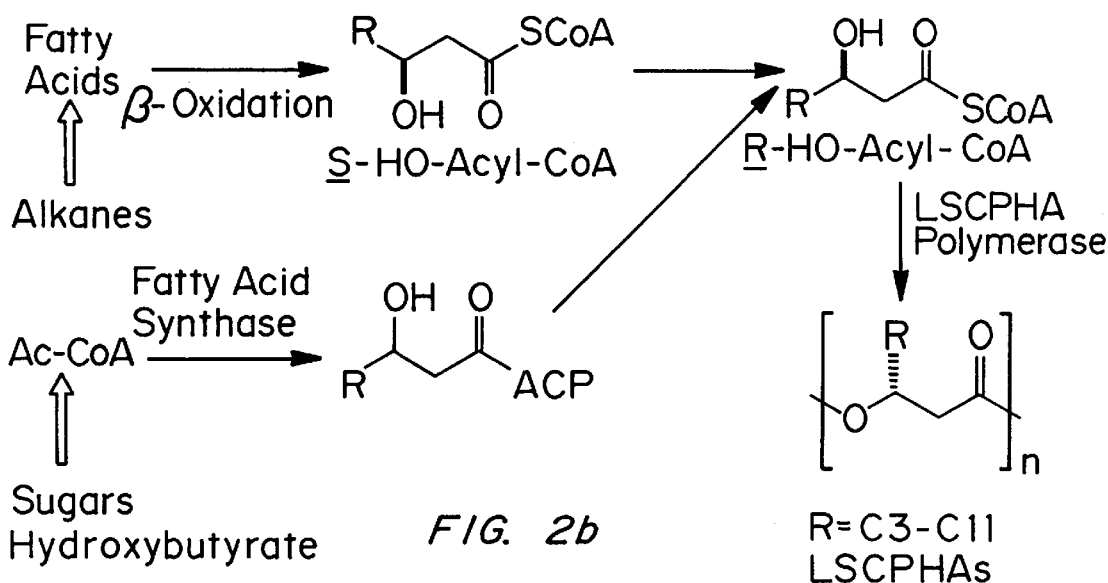
FIG. 2b

METHODS FOR ISOLATING POLYHYDROXYALKANOATES FROM PLANTS

BACKGROUND OF THE INVENTION

The present invention is generally in the area of isolating polyesters from plants.

Polyhydroxyalkanoates (PHAs) are a class of naturally occurring polyesters that are synthesized by numerous organisms in response to environmental stress. For reviews, see Byrom, D., "Miscellaneous Biomaterials", in D. Byrom, Ed., "Biomaterials" MacMillan Publishers, London, 1991, pp. 333–359; Hocking, P. J. and Marchessault, R. H., "Biopolyesters," in G. J. L. Griffin, Ed., "Chemistry and Technology of Biodegradable Polymers", Chapman and Hall, London, 1994, pp. 48–96; Holmes, P. A., "Biologically Produced (R)-3-hydroxyalkanoate Polymers and Copolymers," in D. C. Bassett, Ed., "Developments in Crystalline Polymers," Elsevier, London, Vol. 2, 1988, pp. 1–65; Lafferty et al., "Microbial Production of Poly-β-hydroxybutyric acid," H. J. Rehm and G. Reed Eds., "Biotechnology", Verlagsgesellschaft, Weinheim, Vol. 66, 1988, pp. 135–176; Müller and Seebach, *Angew. Chem. Int. Ed. Engl.*, 32:477–502 (1993); and Steinbüchel, A., "Polyhydroxyalkanoic Acids," Byrom, D., Ed., "Biomaterials", MacMillan Publishers, London, 1991, pp. 123–213.

The PHA biopolymers can be divided into two groups according to the length of their side chains (FIG. 1). Those with short side chains (FIG. 1a), such as polyhydroxybutyrate (PHB), a homopolymer of R-3-hydroxybutyric acid units, are crystalline thermoplastics, whereas PHAs with long side chains (FIG. 1b) are more elastomeric. The former have been known for about seventy years (Lemoigne and Roukhelman, *Annales des Fermentations*, 5:527–536 (1925)) whereas the latter materials were first identified in the early 1980's. De Smet et al., *J. Bacteriol.*, 154:870–878 (1983).

Due to their earlier discovery and their desirable physical properties, the short side chain materials have been more extensively studied. The PHA polymers, which are natural thermoplastics, can be processed using conventional polymer technology and have industrially useful properties, such as biodegradability in soil and marine environments, biocompatibility, and good barrier properties. These characteristics make these materials useful for a wide range of industrial applications.

The PHA polymers may constitute up to 90% of the dry cell weight of bacteria, and are found as discrete granules inside the bacterial cells. These PHA granules accumulate in response to nutrient limitation and serve as carbon and energy reserve materials. Distinct pathways are used by microorganisms to produce each class of these polymers. The pathway leading to the short side chain polyhydroxyalkanoates (SSCPHAs) involves three enzymes, thiolase, reductase and PHB synthase (sometimes called polymerase). Using this pathway, the homopolymer PHB is synthesized by condensation of two molecules of acetyl-Coenzyme A to give acetoacetyl-Coenzyme A, followed by reduction of this intermediate to R-3-hydroxybutyryl-Coenzyme A, and subsequent polymerization (FIG. 2a). The last enzyme in this pathway, the synthase, has a substrate specificity that can accommodate C3–C5 monomeric units including R-4-hydroxy acid and R-5-hydroxy acid units. This biosynthetic pathway is found, for example, in the bacteria *Zoogloea ramigera* and *Alcaligenes eutrophus*.

The biosynthetic pathway which is used to make the long side chain polyhydroxyalkanoates (LSCPHAs) is still partly unknown, however, it is currently thought that the monomeric hydroxyacyl units leading to the LSCPHAs are derived by the β-oxidation of fatty acids and the fatty acid pathway (FIG. 2b). The R-3-hydroxyacylcoenzyme substrates resulting from these routes then are polymerized by PHA synthases that have substrate specificities favoring the larger monomeric units in the C6–C14 range. Long side chain PHAs are produced, for example, by Pseudomonads.

The biosynthesis of PHAs has been studied in a wide range of bacteria at both the biochemical and genetic level, and has been reviewed in Steinbuchel et al., *FEMS Microbiology Reviews*, 103:217–230 (1992). Since the first PHA synthase genes were identified and characterized in 1989 (Peoples and Sinskey, *J. Biol Chem.*, 264:15298–15303 (1989); and U.S. Pat. Nos. 5,229,279, 5,245,023, and 5,250,430 to Peoples and Sinskey), a number of other microbial PHA polymerases have been investigated and their DNA and amino acid sequences published. Steinbuchel et al., *FEMS Microbiology Reviews*, 103:217–230 (1992). More recently, two subunit PHA synthases from *Chromatium vinosum* (Liebersgesell, M. and Steinbuchel, A., *European J. Biochem.*, 209:135–150 (1992); and WO 93/02194) and *Thiocystis violacea* (Liebersgesell, M. and Steinbuchel, A., *Appl. Microbiol. Biotechnot.* 38:493–501 (1993)) have been described.

The genes encoding the enzymes responsible for the production of SSCPHAs in, for example, *Z. ramigera* and *A. eutrophus*, have been isolated and sequenced. Peoples and Sinskey, *Prog. Biotechnol.* 3:51–56 (1987); Peoples et al., *J. Biol. Chem.*, 262:97–102 (1987); Peoples and Sinskey (1989), *J. Biol. Chem.* 264:15298–15303, *J. Biol. Chem.* 264:15293–15297, and *Molecular Microbiol.* 3:349–357; Stater et al., *J. Bacteriol.*, 170:4431–4436 (1988); and Schubert et al., *J. Bacteriol.*, 170:5837–5847 (1988).

PHA producing microorganisms produce PHA to greater than 60% total dry weight and are readily extractable by organic solvent. Lafferty et al., "Microbial Production of Poly-β-Hydroxybutyric Acid", in H. J. Rehm and G. Reed, Eds., "Biotechnology", Verlagsgesellschaft, Weinheim, Vol. 66, 1988, pp. 135–176. In plants, the extraction and recovery of PHA is significantly complicated by the presence of large amounts of plant oil as well as lower percentages of PHA. These complicating factors make the successful extraction, separation and recovery of PHAs from plants more difficult.

There is a need for the development of methods for the large scale processing and purification of polyhydroxyalkanoates from plant biomass. It is therefore an object of the invention to provide methods for processing PHAs from plant biomass on a large scale. It is another object of the invention to provide methods for isolating PHAs from transgenic oil crop plants. It is a further object of the invention to provide methods for processing plant biomass derived from oil seed crop plants such that the recovery of the non-PHA products such as plant oils also is maximized.

SUMMARY OF THE INVENTION

Methods are provided for separating a polyhydroxyalkanoate ("PHA") from plants. In one embodiment, methods are provided for isolating PHAs from a plant biomass derived from transgenic crop plants which contain plant oils. The methods advantageously permit both the oil and the PHAs to be recovered from the plant biomass. To isolate a PHA, in one embodiment, a biomass derived from an oil crop plant is pre-processed, for example by grinding, crushing or rolling. The oil then is extracted from the biomass with a first solvent in which the oil is soluble and in which the PHA is not highly soluble, to separate the oil from the PHA. The essentially oil-free plant biomass then is extracted with a second solvent in which the PHA is soluble, to separate the PHA from the biomass. Alternatively, the PHA-containing biomass is treated with a chemical or biochemical agent, such as an enzyme, to chemically transform the PHA into a PHA derivative. The derivatized PHA then is separated from the mixture using, for example, a physical separation process such as distillation extraction or chromatography Advantageously, using the method, plant oils, PHAs, and PHA derivatives all can be recovered and purified on a large scale from plants such as transgenic oil crop plants.

BRIEF DESCRIPTION OF THE DRAWINGS

FIG. 1a is an illustration of the structure of short side chain polyhydroxyalkanoates.

FIG. 1b is an illustration of the structure of long side chain polyhydroxyalkanoates.

FIG. 2a is an illustration of a biosynthetic pathway for the synthesis of the short side chain polyhydroxyalkanoate, polyhydroxybutyrate.

FIG. 2b is an illustration of a biosynthetic pathway for the synthesis of long side chain polyhydroxyalkanoates.

DETAILED DESCRIPTION OF THE INVENTION

Figure 3:
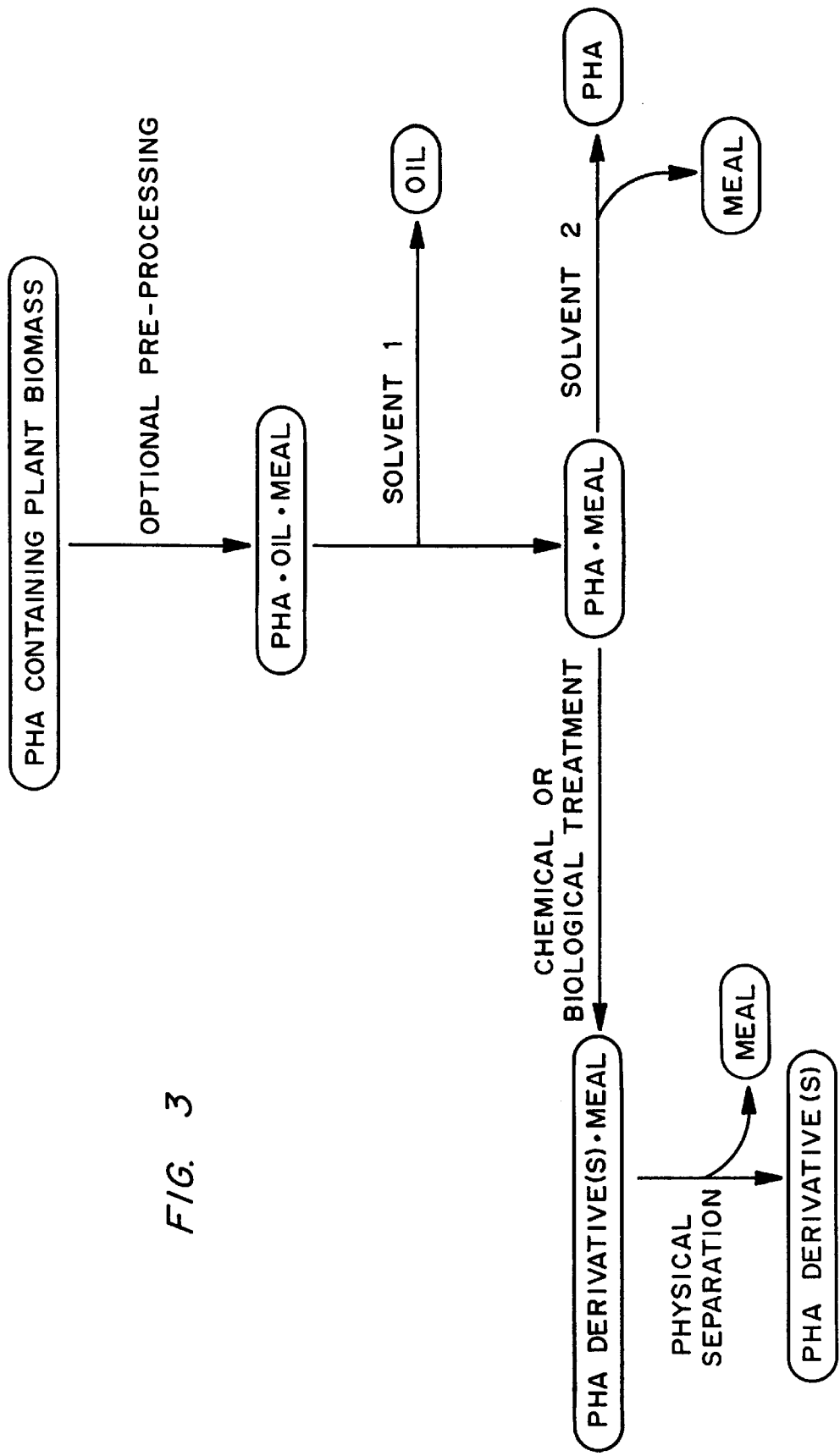
FIG. 3 is flow chart illustrating one embodiment of a process for separating polyhydroxyalkanoates from plants.

Methods are provided for separating polyhydroxyalkanoates ("PHAs") from a plant biomass containing plant oil and meal. PHAs which can be isolated from plant biomass include degradation or other products of PHAs, such as monomers, dimers, oligomers, acids, esters, amides, and lactones, which can be formed from chemical, biochemical or physical treatment during processing of the biomass, or from processes occurring within the plant biomass. In a preferred embodiment, the PHAs are isolated from a biomass derived from a transgenic oil crop plant. In addition to maximizing the recovery of PHA materials, the recovery of commercially useful non-PHA products from the biomass also is maximized. For example, in the case of PHA separation from the seed of an oil-seed plant, the oil and meal also can be isolated and then used commercially.

I. Materials for Isolation of PHAs

A. PHA Materials which can be Isolated

PHA materials which can be isolated from plant biomass include monomers, polymers and other products derived from PHAs including chemically and biologically modified derivatives. The PHA materials are defined in one embodiment as containing one or more units, for example 10 to 100,000 and preferably 100–30,000 units of the following formula I:

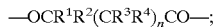

wherein n is 0 or an integer, for example 1–15, and in a preferred embodiment 1–4; and wherein $R^1$, $R^2$, $R^3$, and $R^4$ independently can be hydrocarbon radicals including long chain hydrocarbon radicals; halo- and hydroxy-substituted radicals; hydroxy radicals; halogen radicals; nitrogen-substituted radicals; oxygen-substituted radicals; and/or hydrogen atoms.

As defined herein, the formula $—(CR^3R^4)_n—$ is defined as including but not limited to the following formulas:

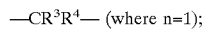

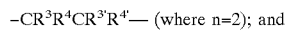

wherein $R^3$, $R^4$, $R^{3'}$, $R^{4'}$, $R^{3''}$, and $R^{4''}$ can be independently hydrocarbon radicals including long chain hydrocarbon radicals; halo- and hydroxy-substituted radicals; hydroxy radicals; halogen radicals; nitrogen-substituted radicals; oxygen-substituted radicals; and/or hydrogen atoms. Thus, formula I includes units derived from 3-hydroxyacids (n=1), 4-hydroxyacids (n-2), 5-hydroxyacids (n=3).

These units may be the same, as in a homopolymer, or be selected from two or more different units, as in a copolymer or terpolymer. The polymers in one embodiment have a molecular weight above 300, for example 300–$10_7$, and in a preferred embodiment, 10,000 to 3,000,000 Daltons. In one embodiment, PHA homopolymers may be isolated such as, for example, polyhydroxybutyrate, polyhydroxyvalerate or polylactic acid. Additionally, PHA copolymers or terpolymers including at least two monomers of a hydroxyalkanoate such as hydroxybutyrate, hydroxyvalerate, hydroxyhexanoate, hydroxyheptanoate, hydroxyoctanoate, hydroxynonanoate and hydroxydecanoate can be isolated. PHAs including monomers and polymers and derivatives of 3-hydroxyacids, 4-hydroxyacids and 5-hydroxyacids can be isolated.

The PHA polymers also may contain or be modified to include other non-hydroxy acid units such as long chain fatty acids, amino acids, carbohydrates, phosphorus and sulfur containing compounds, and triols, such as glycerol. PHA products which can be isolated include derivatives formed upon physical, chemical or biochemical treatment of the biomass or by processes within the biomass including hydroxyacid monomers, dimers, trimers, linear and cyclic oligomers and lactones. PHA derivative products which can be isolated include esters, diols, unsaturated compounds, aldehydes, acids, alcohols, lactones, cyclic and linear esters, amides, and thioesters of polyhydroxyalkanoates or of a monomer derived from the polyhydroxyalkanoate.

Representative PHA products which can be isolated from plant biomass include:

esters defined by the formula: $HOCR^1R^2(CR^3R^4)_nCO_2R^5$;

amides defined by the formula: $HOCR^1R^2(CR^3R^4)_nCONR^5R^6$;

thioesters defined by the formula: $HOCR^1R^2(CR^3R^4)_nCOSR^5$;

acids defined by the formula: $HOCR^1R^2(CR^3R^4)_nCO_2H$;

ethers defined by the formula: $R^6OCR^1R^2(CR^3R^4)_nCO_2R^5$;

esters defined by the formula: $R^6CO_2CR^1R^2(CR^3R^4)_nCO_2R^5$;

unsaturated compounds defined by the formulas: $R^1R^2C=CR^3(CR^4R^5)_nCO_2R^6$; and $R^1R^2R^3CC(R^4)=C(R^5)CO_2R^6$;

diols defined by the formula: $HOCR^1R^2(CR^3R^4)_nCH_2OH$;

lactones or macrolides, defined by the formula:

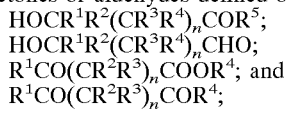

where x is an integer, for example from 1 to 10; and ketones or aldehydes defined by the formula:

$HOCR^1R^2(CR^3R^4)_nCOR^5$;
$HOCR^1R^2(CR^3R^4)_nCHO$;
$R^1CO(CR^2R^3)_nCOOR^4$; and
$R^1CO(CR^2R^3)_nCOR^4$;

wherein n is 0 or an integer; and wherein $R^1$, $R^2$, $R^3$, $R^4$, $R^5$ and $R^6$ are each independently hydrocarbon radicals including long chain hydrocarbon radicals, halo- and hydroxy-substituted radicals, hydroxy radicals, halogen radicals, nitrogen-substituted radicals, oxygen-substituted radicals, and hydrogen atoms; and wherein —$(CR^2R^3)_n$— is defined as described above.

Commercially useful monomer PHA products such as 3-hydroxybutyric acid or crotonic acid, or alkyl esters thereof, including methyl-3-hydroxybutanoate, ethyl-3-hydroxybutanoate, propy 3-hydroxybutanoate and butyl-3-hydroxybutanoate also can be isolated The PHA derived hydroxy acid monomers, in addition to the higher molecular weight forms, are a source of valuable chemicals that can be used commercially either with or without further modification.

As used herein, the term "PHA materials", or "PHAs" or "polyhydroxyalkanoates" refers to monomers, polymers and other PHA-based materials originally present in the biomass prior to processing, and products formed during processing such as products formed from degradation or processes occurring within the plant biomass or derivative products formed by treatment of the biomass with chemical or biological agents to cause a chemical transformation.

B. Plant Sources from which PHAs can be Isolated

Plant Species

PHAs and PHA products can be isolated from plant biomass derived from plants such as soybean, cotton, coconuts, groundnuts, rapeseed, sunflower seed, olive, palm, sesame seed, linseed, castor, safflower seed, tobacco and potato. In a preferred embodiment, the biomass can be derived from an oil crop plant, particularly rapeseed, sunflower seed, safflower seed, linseed and soybean. In the processing, the plant oil in the seed crop plants can be isolated and recovered in addition to the PHA polymers. Plant oils typically make up 10–50% of the seed by weight. The worldwide demand for plant oil is considerable. The methods for processing the plant biomass can be tailored based on the properties of the particular PHA polymer or derivative being isolated, and based on the type of plant crop and the plant components being extracted.

Production of Transgenic Plants

The use of transgenic oil crop plants offers many advantages. Transgenic crop plants for production of PHAs can be obtained using methods available in the art. Transgenic plant crop production can produce PHA polymers at both a price and a scale that is competitive with petrochemical derived plastics. Transgenic plant derived PHA polymers or their derivatives can be processed and separated from plant biomass in commercially useful forms. The location of the PHA in the plant crop (e.g., leaf, seed, stem or combinations thereof) can be varied to maximize the yield of PHA from the plant.

The genes encoding the enzymes responsible for the production of short side chain PHAs in, for example, Z. *ramigera* and *A. eutrophus*, have been identified, isolated and sequenced. Peoples and Sinskey, *Prog. Biotechnol.* 3:51–56 (1987); Peoples et al., *J. Biol. Chem.*, 262:97–102 (1987); Peoples and Sinskey (1989), *J. Biol. Chem.* 264:15298–15303, *J. Biol. Chem.* 264:15293–15297, and *Molecular Microbiol.* 3:349–357; Slater et al., *J. Bacteriol.*, 170:4431–4436 (1988); and Schubert et al., *J. Bacteriol.*, 170:5837–5847 (1988), the disclosure of which is incorporated herein by reference. In *A. eutrophus*, they were found to form an operon, phbC-phbA-phbB genes, coding for the short side chain PHA synthase, thiolase, and reductase, respectively. For the long side chain PHAs, the synthase enzymes in the Pseudomonas organism were found to be encoded by the pha focus. This locus includes two closely related PHA synthase genes, phaA and phaC, as well as a depolymerase gene which is the product of the phaB gene.

Methods which can be used for producing PHA polymers in transgenic crop species are described in: U.S. Pat. Nos. 5,245,023 and 5,250,430; WO 91/00917; WO 92/19747; WO 93/02187; WO 93/02194; WO 94/11519; WO 94/12014; WO 94/23027; WO 95/05472; Poirier et al., *Science*, 256:520–523 (1992), Poirier et al., *BiolTechnol.*, 13:142–150 (1995) and Nawrath et al., *Proc. Natl. Acad. Sci. USA,* 91:12760–12764 (1994), the disclosures of which are incorporated herein by reference To form a transgenic crop species, a gene encoding a PHA synthase is transferred from a microorganism into plant cells to obtain the appropriate level of production of the PHA synthase enzyme. The gene may be derived from a microorganism such as Acinetobacter, Aeromonas, Alcaligenes, Azotobacter, Bacillus, Brevibacterium, Corynebacterium, Chromatium, Flavobacterium, Halobacterium, Pseudomonads, Nocardia, Rhodococcus, Thiocystis, Streptomyces, Streptococcus or Zoogloea. Additional PHA biosynthetic genes also can be provided, for example, an acetoacetyl-CoA reductase gene or other genes encoding enzymes required to synthesize the substrates for the PHA synthase enzymes. The expression in different plant tissues or organelles can be controlled using methods known to those skilled in the art. Gasser and Fraley, *Science*, 244:1293–1299 (1989), the disclosure of which is incorporated herein by reference, and references cited therein. PHB has been produced in genetically engineered plant systems by standard techniques. Poirer, Y. et al., *Science*, 256:520–523 (1992); Poirier, Y. et al., *Bio/Technol.*, 13:142–150 (1995); and Nawrath, C. et al., *Proc. Natl. Acad. Sci. USA,* 91:12760–12764 (1994), the disclosures of which are incorporated herein by reference.

In a preferred embodiment, the PHA content of the plant biomass prior to extraction is at least 1% by weight of the dry weight of biomass, more preferably 5–95% by weight of the dry weight of biomass, and in another preferred embodiment between about 5–60% by weight of the dry weight of biomass, most preferably 10–60%. Preferably, at least 24% of the PHA is recovered in the process separate from oil.

II. Methods for Isolation of PHAs from Plants

A. Pre-processing of the Plant Biomass

The PHA-containing plant biomass, for example, a transgenic oil crop plant containing a heterologous PHA synthase gene, is cultivated and harvested. The plant biomass may be pre-processed prior to extraction of the PHA polymers using methods available in the art, such as agitation, heating, cooling, pressure, vacuum, sonication, centrifugation, and/or radiation. As used herein, the term "plant biomass" refers to plant components including seeds, leaf, stalk and stem. Additionally, the plant biomass can be pre-processed using any one or more combinations of procedures including drying, dehulling, cleaning, ageing, cleaning, weighing, cracking, flaking, pressing, rolling, grinding, cooking, crushing, settling, and/or filtering. The use of these procedures for separating oil from meal in the processing of oil bearing plants is described in "Oil Crops of the World," G. Röbbblen et al., Eds., McGraw-Hill Publishing Company, 1989, Chapter 11, the disclosure of which is incorporated herein by reference.

B. Extraction of Plant Biomass

The PHA monomers, polymers and derivatives can be removed from the plant biomass using suitable means including solvent extraction and/or washing, aqueous extraction and/or washing, crushing, temperature treatment, enzymatic treatment, centrifugation, supercritical fluid extraction, high and/or reduced pressure treatment, chromatography, distillation, melting, or treatment with reagents to facilitate separation of the PHA materials.

Methods for extracting the oil from the preprocessed material available in the art also may be used, such as oil expeller pressing where the oil is mechanically squeezed from the oil bearing material, and prepressing solvent extraction where a portion of the oil is removed by expellers and the remainder by extraction with an organic solvent, such as a hydrocarbon, for example, hexane. Additionally, supercritical gases including carbon dioxide and propane can be used. Other methods include direct solvent extraction where the oil is removed directly from conditioned seed with an organic solvent; propane refining to separate fat; and fat splitting involving hydrolysis of fat or oil with water to produce glycerol and fatty acid. "Oil Crops of the World," G. Röbblen et al., Eds., McGraw-Hill Publishing Company, 1989; "Liquid Extraction," R. Treybal, Ed., McGraw-Hill Book, New York, 1951; and "World Oilseeds: Chemistry, Technology, and Utilization," D. K. Salunkhe et al., Eds., Van Nostrand Reinhol, New York, 1992.

Extraction of Oil from Plant Biomass

One preferred method for isolating the PHAs from a plant biomass is illustrated in the flow chart of FIG. 3. In the process, the PHA containing plant biomass first optionally is pre-processed as described above. The pre-processed or unprocessed PHA containing plant biomass then is extracted in a solvent in which the oil is soluble, and in which the PHA and the meal are not highly soluble, to remove the majority or all of the oil from the PHA containing plant biomass. The solvent is selected such that it is a good extractant for the oil and a poor extractant with low solubility for the PHA and the plant meal. Extraction of the PHA-oil-meal mixture, as illustrated in the flow chart of FIG. 3, produces an oil fraction essentially free of PHA (for example including less than about 10% by weight of PHA) and an essentially oil free PHA-meal mixture (including for example, less than about 10% oil by weight). The PHA-meal mixture then is extracted with a second solvent in which the PHAs are soluble, to obtain purified PHA materials. Alternatively, the PHA-meal mixture can be treated chemically or enzymatically to produce PHA derivatives which are then isolated from the meal, as illustrated in FIG. 3.

The first solvent which is used to extract the oil from the plant biomass is selected based on its ability to solubilize the oil. Preferably, a solvent is used in which the oil is soluble and in which the PHA and plant material is not highly soluble. Suitable solvents include hydrocarbons, such as propane, butane, pentane, hexane, heptane, octane, nonane and decane. As used herein the term "solvent" includes solvents as well as solvent mixtures, such as mixtures of hydrocarbons. Preferably, the first solvent is chosen wherein the PHA is soluble to less than 1%, most preferably less than 0.1% and the oil is soluble to more than 10% (w/v, ambient temperature).

To isolate the PHA and oil components from the biomass, solvents used in the extractions are selected which exploit the differences in the physical nature and solubility characteristics of the PHA and oil components of the biomass. The isolation steps are tailored depending on the particular PHA, plant host or PHA/plant host combination. For example, in the extraction of PHB and LSCPHA, different solvents or solvent combinations are used in their extraction from PHA-containing transgenic plant biomass based on their solubility.

In the embodiment where the PHA is separated from the PHA-meal product by treatment with a second solvent, the second solvent (solvent 2 in FIG. 3) is selected based on its capability of being a good extractant for the PHA and a poor extractant for the meal. Solvents which can be used include solvents or solvent mixtures including chlorinated organic solvents such as chloroform, methylene chloride, dichloroethane, trichloroethane, tetrachloroethane and dichloroacetate. For example, hydrocarbon stabilized chloroform can be used. Other solvents which have been used to extract PHAs from microbial sources which may be used include alkyl carbonates, such as propylene carbonate and ethylene carbonate, trifluoroethanol, acetic anhydride, dimethylformamide, ethylacetoacetate, triolein, toluene, dioxane, tetrahydrofuran, diethylether, pyridine, hydroxyacids and alcohols having more than 3 carbon atoms, as well as mixtures thereof. Lafferty et al., "Microbial Production of Poly-$\beta$-Hydroxybutyric Acid," in H. J. Rehm and G. Reed, Eds., "Biotechnology", Verlagsgesellschaft, Weinheim, Vol. 66, 1988, pp. 135–176. In a preferred embodiment, the second solvent is a chlorinated organic solvent or an alkyl carbonate. Additionally, in a preferred embodiment, the first and second solvents have boiling points between ambient temperature and 400° C., more preferably between 30° C. and 250° C.

The solvent extraction steps also can be conducted using supercritical fluid extraction, wherein a gas is used such as ethylene, propylene, propylene oxide, butane or carbon dioxide. In a preferred embodiment, the gas has a boiling point between –250° C. and ambient temperature, preferably between –150° C. and –20° C. The PHA also may be extracted in a molten state.

In an alternative embodiment, as illustrated in the flow chart of FIG. 3, the PHA-meal mixture is treated with a chemical or biochemical agent, such as an enzyme, to chemically transform the PHAs into PHA derivatives as described in detail below. The PHA derivatives then are separated from the plant biomass if necessary, using one or more subsequent physical separation steps such as distillation, extraction, centrifugation, filtration or chromatography.

Extraction of PHA and Oil.

Figure 4:
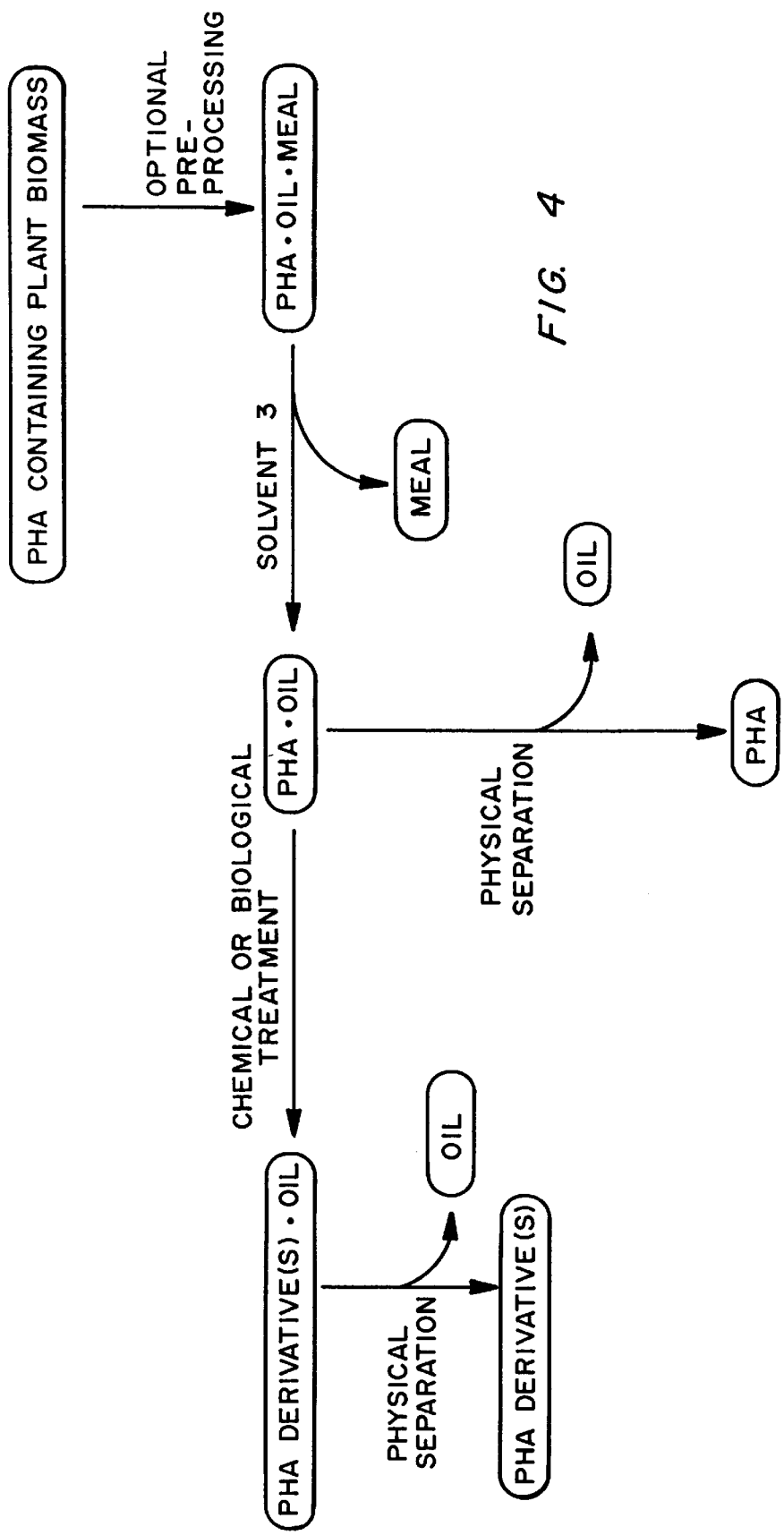
FIG. 4 is a flow chart illustrating another embodiment of a process for separating polyhydroxyalkanoates from plants.

In another embodiment, shown in the flow chart of FIG. 4, the PHA containing plant biomass optionally first is pre-processed as described above. The pre-processed or unprocessed PHA containing plant biomass then is solvent extracted in a solvent in which the oil and the PHAs are soluble, and in which the meal is not highly or is poorly soluble, to essentially remove the oil and the PHAs from the plant meal, such that, for example, less than about 10% of oil and PHAs by weight remain in the plant meal. The solvent used in this process is selected such that it is a good extractant for the PHAs and oil, and a poor extractant for the meal. The PHA materials in the PHA-oil product then are further separated from the oil by a physical separation step, such as distillation, or by further exploitation of differences in solubility between the PHA and oil.

Alternatively, the PHA-oil product may be modified by chemical or biological treatment to provide a PHA derivative(s)-oil product as described below (as shown in FIG. 4). The PHA derivative component of the latter may be subsequently purified by physical processing, including distillation, solvent extraction, washing, precipitation, centrifugation, supercritical fluid extraction, filtration, and chromatography.

Solvents which may be used to extract the oil-PHA component from the plant biomass include chlorinated organic solvents, for example, chloroform, methylene chloride, di-, tri-, tetra-chloroethane and dichloroacetate, alkyl carbonates such as propylene carbonate and ethylene carbonate, trifluoroethanol, acetic anhydride, dimethylformamide, ethylacetoacetate, triolein, acetic acid, toluene, alcohols, hydroxyacids, dioxan, tetrahydrofuran, diethylether, and/or pyridine. The solvent also may consist of or may include hydrocarbons such as hexane, heptane, octane, nonane or decane or mixtures thereof. Preferred solvents are those having boiling points between ambient temperature and 400° C., preferably between 30° C. and 250° C. Preferably, such solvents have solubility for both PHA and oil components of at least 5% (w/v, ambient temperature), and are chosen depending upon the structure of the PHA defined in FIG. 1. The PHA material also can be extracted in the molten state. The choice of solvent will depend on the choice of plant from which the biomass is derived and the solubility properties of the PHAs, derivatives and oils being separated.

As illustrated in the flow chart of FIG. 4, the extracted PHA-oil also can be separated by chemical modification to form a PHA derivative-oil product, by treatment with a chemical or biological agent, such as an enzyme which degrades the PHA material, as described in detail below. The PHA derivative then is separated from the PHA derivative-oil mixture using, for example, a physical process such as distillation, extraction, centrifugation, supercritical fluid extraction, preparation filtration, and/or chromatography. Further refining of the essentially oil free PHA can be carried out by standard procedures known to those skilled in the art.

III. Synthesis of PHA Derivatives

As described above, during the processing, the PHA materials in the biomass can be derivatized by physical, chemical or enzymatic conversion into derivatives, prior to their isolation, to faciliate the isolation of the materials, or to produce a desired derivative product. PHA derivatives which can be formed include acids, esters, oligomers, cyclic oligomers, lactones, macrolides, amides, amines, thioesters, diols, and unsaturated compounds, which can be formed using methods available in the art. Griesbeck, A. and Seebach, D., *Helv. Chim. Acta* 70:1320–1325 (1987); Plattner, D. A., *Helv. Chim. Acta,* 76:2004–2033 (1993); Seebach, D. et al., "Biological-Chemical Preparation of 3-Hydroxycarboxylic Acids and Their Use in EPC-synthesis," W. Bartmann and K. B. Sharpless, Eds., "Stereochemistry of Organic and Bioorganic Transformations," VCH, Weinheim, 1987, pp. 85–126; and Seebach, D. et al., *Chimia,* 44:112–116 (1990); *Org. Synth.,* 71:3947 (1992); *Angew. Chem. Int. Ed. Eng.,* 434–435 (1992); and *Helv. Chim. Acta,* 77:1099–1123 (1994), the disclosures of which are incorporated herein by reference. Additional methods for derivatizing esters, which may be used to form PHA polyesters are known to those skilled in the art.

Chemical agents which can be used to modify the PHA materials in the processing of the biomass include, for example, acids, bases, detergents, chelator, an oxidizing or reducing agent, a nucleophilic or electrophilic reagent, metal ions, aqueous solutions or organic solutions, and free radicals. Other chemical agents which can be used include hydrogen peroxide, hypochlorite, ozone and alkyl peroxides. The chemical transformation can be, for example, a chemical reaction such as an esterification, transesterification, hydrolysis, saponification, aminolysis, thiolysis, etherification, silylation, addition, elimination, rearrangement, or condensation. The chemical agents can be used, for example, to produce derivatives with a molecular weight less than that of the PHA starting materials in the plant biomass. Additionally, the PHA materials can be modified by physical treatment such as heat, cold or agitation.

The PHA materials also can be chemically modified during processing by treatment of biomass materials such as PHA-meal or PHA-oil mixtures with a biological agent such as an enzyme, which for example, degrades the biomass or the PHA material. Enzymes which can be used include PHA depolymerases, proteases, nucleases, lipases, hydratases, phosphorylases, cellulases and/or glycosidases. The PHA polymers may be converted to oligomers, monomers, dimers, trimers, or other derivatives. The PHA functionality may also be converted to non-PHA chemical functionality.

IV. Applications

The PHAs isolated as described herein can be used in a wide variety of different applications. In one embodiment, the isolated PHAs can be used to form a latex. PCT WO 91/13207 discloses the use of polymers or copolymers of β-hydroxybutyrate and β-hydroxyvalerate in the form of a latex, i.e., as an aqueous suspension of non-crystalline, amorphous particles. The latex can be used, for example, to form films or coated papers which are biodegradable and recyclable. Methods for forming a PHA latex from purified crystalline PHAs are described in PCT WO 94/07940, the disclosure of which is incorporated herein by reference in the method, a purified solution of PHA in an organic solvent, which can be obtained as described herein, is emulsified in an aqueous solution including a surfactant, to form an amorphous latex. Thus, the methods disclosed herein provided purified PHAs which can be used in a variety of industrial and biomedical applications such as the formation of PHA latex materials.

The invention will be further understood from the following non-limiting examples.

EXAMPLE 1

Extraction of Polyhydroxybutyrate from Plant Biomass.

The process illustrated in FIG. 3 was used to isolate polyhydroxybutyrate (PHB) from plant biomass by extraction with hexane (solvent 1) to remove the oil followed by extraction with hydrocarbon stabilized chloroform (solvent 2) to isolate PHB.

A sample of rapeseed (32 g) containing approximately 40 weight % oil was admixed with 6 g of PHB powder (Aldrich) and ground using an electric food grinder. This sample is representative of a transgenic oil seed containing 34% by weight oil and 16% by weight of PHB. The mixture was continuously extracted with 300 mL hexane (solvent 1) in a soxhlet apparatus for 6 hours after which time the sample was allowed to cool providing an organic solvent phase and a solid meal. The organic solvent was concentrated to yield a yellow oil (11.8 g, 31% by weight of the admixture). NMR analysis indicated that the oil contained no PHB. This result indicates that PHB-free oil can be readily recovered at greater than 90% yield from PHA containing plant biomass. A portion of the solid meal (7.7 g) was then further extracted with 120 mL of hydrocarbon stabilized chloroform (Solvent 2) for 22 hours in a soxhlet apparatus. Evaporation of the chloroform solution resulted in the formation of a yellow/white plastic film weighing 1.15 g. A portion of the crude PHB film (227 mg) was washed with three, one mL portions of hexane. After air drying, the PHB film (86 mg) was off-white in color. NMR analysis of this film indicated that it was essentially pure PHB. The recovery of PHB film represents a 24% yield based on the original PHB content of the admixture.

EXAMPLE 2

Extraction of a PHB Derivative from Plant Biomass.

The process illustrated in FIG. 3 was used to isolate polyhydroxybutyrate (PHB) from plant biomass by extraction of plant biomass with hexane (solvent 1) to remove the oil fraction followed by chemical treatment and then physical separation of the PHB in derivative form.

A portion of the PHB containing residual meal (2.32 g) from Example 1 was heated at reflux for 15.5 hours with n-butanol (25 mL) and concentrated sulfuric acid (0.33 mL). To the resultant black mixture was added saturated sodium bicarbonate (20 mL), brine (20 mL) and ethyl acetate (50 mL). The mixture was shaken in a separatory funnel and the phases were separated. The organic phase was filtered through a pad of celite, washed with brine, treated with a small amount of activated charcoal, filtered, and concentrated to a dark oil. This material was distilled under reduced pressure. The fraction distilling at 49–53° C. and 0.25 torr was collected to yield a slightly yellow colored liquid (0.47 g). NMR analysis of this material confirmed that it was butyl 3-hydroxybutyrate. The amount of material recovered represents a 46% yield of derivatized PHB based on the amount of PHB contained in the residual meal.

EXAMPLE 3

Extraction of PHAs from Rapeseed

PHA was extracted in polymer form from rapeseed using the process of FIG. 4 as follows. A sample of rapeseed (20 g) containing approximately 40% by weight oil was admixed with small pieces of PHO, a copolymer including approximately 94% 3-hydroxyoctanoic acid and approximately 6% 3-hydroxyhexanoic acid (5.43 g, isolated from *Pseudomonas putida*) and ground using an electric food grinder. This sample is representative of a transgenic oil seed containing 31% by weight oil and 21% by weight of PHO. The mixture was continuously extracted with 300 mL hexane (Solvent 1) in a soxhlet apparatus for 12 hours. The sample was allowed to cool and was filtered to provide an organic solvent phase and a solid meal (11.02 g after air drying). The solvent phase was concentrated to yield a yellow, very viscous gel-like material (12.92 g, 51% by weight of the admixture). Upon standing, this material set into a yellow, plastic-like solid. NMR analysis indicated that the material contained PHO and rapeseed oil. These results indicate that PHO oil mixture can be readily recovered at greater than 90% yield from PHA containing plant biomass. The PHA/oil mixture obtained was suitable for further purification.

Further purification was conducted as follows. A portion of the yellow, plastic-like material (0.136 g, approximately 41% wt PHO, 1.1×0.2 cm) was washed with 2 ml of n-propanol. After slowly swirling at room temperature for 3 days, the supernatant was removed, and the residual solid was washed overnight with 2 ml of methanol. The methanol wash was combined with the propanol wash and concentrated to yield a yellow oil (0.0876 g). After drying under vacuum, the residual solid polymer (0.048 g) was semitransparent and almost colorless. This represents an 84% yield of PHO from the original rapeseed/PHO mixture. NMR analysis of the purified polymer showed that it was PHO (approximately 95% purity) containing a small amount of rapeseed oil. G.C. analysis showed a 10 fold reduction of major contaminants relative to the yellow, plastic-like material initially isolated by hexane extraction.

EXAMPLE 4

Isolation of a PHA Derivative from Plant Biomass

The yellow PHO containing plastic-like material obtained prior to further purification, as described in Example 3, was further purified in derivative form by chemical treatment and physical separation A portion of the partially purified PHO containing plastic material (2.75 g, containing approximately 40% by weight PHO) isolated by hexane extraction from Example 3 was dissolved in n-butanol (50 mL) with heating. Concentrated sulfuric acid (0.7 mL) was added and the mixture was heated at reflux for 20 hours. After cooling to room temperature, saturated sodium carbonate (4 mL) was added to make the mixture basic to pH paper. The reaction mixture was filtered, the phases were separated and the organic layer washed with brine (2×30 mL). The organic phase was concentrated to about 10 mL, dissolved in chloroform (50 mL), dried over magnesium sulfate, filtered and concentrated under vacuum to a yellow oil (2.75 g). This material was distilled under reduced pressure. The fraction distilling at 93–97° C. and 0.45 torr was collected to yield a clear, colorless liquid (0.41 g). The amount of material recovered represents a 25% yield of derivatized PHO based on the amount of PHO contained in the plastic-like starting material. NMR analysis of this material indicated that it is butyl 3-hydroxyoctanoate of approximately 95% purity and that it contains a very small amount of unsaturated material.

Modifications and variations of the present invention will be obvious to those skilled in the art from the foregoing detailed description. Such modifications and variations are intended to come within the scope of the following claims.

We claim:

1. A method for separating a polyhydroxyalkanoate ("PHA") from a plant biomass comprising plant oil and meal, the method comprising extracting the plant biomass with a solvent to essentially remove the oil from the biomass, and then separating the PHA from the plant biomass.

2. The method of claim 1 wherein the plant biomass is derived from a transgenic plant.

3. The method of claim 1 further comprising derivatizing the PHA prior to separating the PHA from the biomass.

4. The method of claim 1 wherein the separated PHA comprises one or more units having the formula:

$$-OCR^1R^2(CR^3R^4)_nCO-$$

wherein n is 0 or an integer; and wherein $R^1$, $R^2$, $R^3$, and $R^4$ each are independently selected from the group consisting of hydrocarbon radicals, halo- and hydroxy-substituted radicals, hydroxy radicals, halogen radicals, nitrogen-substituted radicals, oxygen-substituted radicals and hydrogen atoms.

5. The method of claim 4 wherein the separated PHA is selected from the group consisting of monomers, dimers, linear and cyclic oligomers, and lactones of the units.

6. The method of claim 3 wherein the separated PHA is selected from the group consisting of esters defined by the formula: $HOCR^1R^2(CR^3R^4)_nCO_2R^5$;

amides defined by the formula: $HOCR^1R^2(CR^3R^4)_nCONR^5R^6$;

thioesters defined by the formula: $HOCR^1R^2(CR^3R^4)_nCOSR^5$;

acids defined by the formula: $HOCR^1R^2(CR^3R^4)_nCO_2H$;

ethers defined by the formula: $R^6OCR^1R^2(CR^3R^4)_nCO_2R^5$;

esters defined by the formula: $R^6CO_2CR^1R^2(CR^3R^4)_nCO_2R^5$;

unsaturated compounds, defined by the formulas: $R^1R^2C=CR^3(CR^4R^5)_nCO_2R^6$; and $R^1R^2R^3CC(R^4)=C(R^5)CO_2R^6$;

diols defined by the formula: $HOCR^1R^2(CR^3R^4)_NCH_2OH$;

lactones or macrolides defined by the formula:

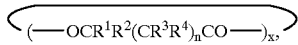

wherein x is an integer; and ketones or aldehydes defined by the formulas:
$HOCR^1R^2(CR^3R^4)_nCOR^5$;
$HOCR^1R^2(CR^3R^4)_nCHO$;
$R^1CO(CR^2R^3)_nCOOR^4$; and
$R^1CO(CR^2R^3)_nCOR^4$;

wherein n is 0 or an integer; and wherein $R^1$, $R^2$, $R^3$, $R^4$, $R^5$ and $R^6$ are each independently selected from the group consisting of hydrocarbon radicals, halo- and hydroxy-substituted radicals, hydroxy radicals, halogen radicals, nitrogen-substituted radicals, oxygen-substituted radicals, and hydrogen atoms.

7. The method of claim 1 comprising
a) providing a plant biomass containing a PHA;
b) pre-processing the plant biomass to obtain a mixture containing PHA, oil and plant meal;
c) extracting oil from the mixture with a first solvent in which the oil is soluble and in which the PHA is not highly soluble, to obtain a residual meal mixture comprising PHA; and
d) extracting the residual meal mixture obtained in step c) with a second solvent in which the PHA is soluble, to separate PHA from the biomass.

8. The method of claim 1 comprising
a) providing a plant biomass containing a PHA;
b) pre-processing the plant biomass to produce a mixture containing PHA, oil and plant meal;
c) extracting oil from the mixture with a first solvent in which the oil is soluble and in which the PHA is not highly soluble, to obtain a residual meal mixture comprising PHA;
d) treating the residual meal mixture comprising PHA, obtained in step c), with at least one chemical or biochemical agent, to chemically derivative the PHA; and
e) separating derivatized PHA from the residual meal mixture obtained in step d).

9. The method of claim 7 or 8 wherein step b) comprises pre-processing the plant biomass using one or more processes selected from the group consisting of drying, dehulling, cleaning, ageing, cleaning, weighing, cracking, flaking, pressing, rolling, grinding, cooking, crushing, settling and filtering.

10. The method of claim 7 or 8 wherein the first solvent comprises a hydrocarbon.

11. The method of claim 10 wherein the first solvent comprises a hydrocarbon selected from the group consisting of propane, butane, pentane, hexane, heptane, octane, nonane and decane.

12. The method of claim 7 wherein the second solvent is selected from the group consisting of a chlorinated organic solvent, an alkyl carbonate, an alcohol, and a hydroxyacid and mixtures thereof.

13. The method of claim 12 wherein the second solvent comprises a chloronated organic solvent selected from the group consisting of chloroform, methylene chloride, dichloroethane, trichloroethane, tetrachloroethane and dichloroacetate.

14. The method of claim 7 wherein the second solvent comprises a composition selected from the group consisting of a propylene carbonate, ethylene carbonate, trifluoroethanol, acetic anhydride, acetic acid, dimethylformamide, ethylacetoacetate, triolein, toluene, dioxan, tetrahydrofuran, diethylether and pyridine.

15. The method of claim 8 wherein, in step d), the residual meal mixture comprising PHA is treated with at least one chemical agent selected from the group consisting of an acid, a base, a detergent, an oxidizing agent, a chelating agent, a reducing agent, a nucleophilic reagent, an electrophilic reagent, a metal ion, an aqueous solution and an organic solution.

16. The method of claim 8 wherein the PHA is derivatized by a chemical transformation selected from the group consisting of an esterification, transesterification, hydrolysis, saponification, aminolysis, thiolysis, etherification, silylation, addition, elimination, rearrangement, and a condensation.

17. The method of claim 8 wherein the biochemical agent is an enzyme.

18. The method of claim 17 wherein the enzyme is selected from the group consisting of a depolymerase, protease, nuclease, lipase, phosphorylase and a glycosidase.

19. The method of claim 8 wherein, in step e), the derivatized PHA is separated by a physical process selected from the group consisting of distillation, extraction, centrifugation, filtration, and chromatography.

20. The method of claim 7 or 8 wherein the first and second solvents each have boiling points between 30° C. and 250° C.

21. The method of claim 7 or 8 further comprising using a third solvent to precipitate the separated PHA.

22. The method of claim 1 wherein the biomass is derived from a plant source selected from the group consisting of soybean, cotton, coconuts, groundnuts, rapeseed, sunflower seed, olive, palm, sesame seed, linseed, castor, safflower seed, tobacco and potato.

23. The method of claim 4 wherein the separated PHA includes one or more of the same or different units selected from the group consisting of hydroxybutyrate, hydroxyvalerate, hydroxyhexanoate, hydroxyheptanoate, hydroxyoctanoate, hydroxynonanoate, and hydroxydecanoate.

24. The method of claim 1 wherein the separated PHA is selected from the group consisting of 3-hydroxybutyric acid, crotonic acid and alkyl esters thereof.

25. The method of claim 2 wherein the plant biomass is derived from a plant containing a heterologous PHA synthase gene derived from a microorganism selected from the group consisting of Acinetobacter, Aeromonas, Alcaligenes, Azotobacter, Bacillus, Brevibacterium, Corynebacterium, Chromatium, Flavobacterium, Halobacterium, Pseudomonads, Nocardia, Rhodococcus, Thiocystis, Streptomyces, Streptococcus and Zoogloea.

26. The method for separating a polyhydroxyalkanoate ("PHA") from a plant biomass comprising plant oil, the method comprising extracting a plant biomass with a solvent, in which the oil and PHA are soluble, to essentially remove oil and PHA from the biomass, and then separating PHA from the oil.

27. The method of claim 26 wherein the plant biomass is derived from a transgenic oil crop plant.

28. The method of claim 26 wherein the method comprises
a) providing a plant biomass containing a PHA;
b) pre-processing the plant biomass to obtain a mixture of PHA, oil and plant meal;
c) extracting oil and PHA from the mixture with a first solvent in which the oil and the PHA are soluble and in which the meal is not highly soluble; and
d) separating the PHA from the oil.

29. The method of claim 28 wherein the PHA is separated from the oil in step d) by treating the PHA-oil mixture with a chemical or biochemical agent, thereby to chemically derivatize the PHA, and separating derivatized PHA from the oil.

30. The method of claim 28 wherein the solvent is selected from the group consisting of a chloronated organic solvent, an alkylcarbonate, an alcohol, a hydroxyacid and a hydrocarbon, and mixtures thereof.

31. The method of claim 28 wherein the solvent is selected from the group consisting of hexane, trifluoroethanol, acetic anhydride, dimethylformamide, ethylacetoacetate, triolein, acetic acid, toluene, dioxane, tetrahydrofuran, diethylether and pyridine.

32. The method of claim 29 wherein the biochemical agent is an enzyme selected from the group consisting of a PHA depolymerase, protease, lipase, esterase, hydratase and a phosphorylase.

33. The method of claim 7, 8, 28 or 29 wherein the separated PHA includes a functional group selected from the group consisting of esters, amides, thioesters, acids, ethers, esters, unsaturated compounds, diols, ketones and aldehydes.

34. The method of claim 7, 8, 28 or 29 wherein the separated PHA includes one or more units selected from the group consisting of a 3-hydroxyacid, a 4-hydroxyacid and a 5-hydroxyacid.

35. The method of claim 7 or 28 wherein the separated PHA is separated in an organic solvent; and wherein the method further comprises:
emulsifying the PHA in the organic solvent in an aqueous solution containing a surfactant, thereby to form a PHA latex.

* * * * *